US011270798B2

(12) United States Patent
Patil et al.

(10) Patent No.: US 11,270,798 B2
(45) Date of Patent: Mar. 8, 2022

(54) CENTRAL SIGNAL SEGREGATION SYSTEM

(71) Applicant: KONINKLIJKE PHILIPS N.V., Eindhoven (NL)

(72) Inventors: Ravindra Balasaheb Patil, Bangalore (IN); Krishnamoorthy Palanisamy, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 514 days.

(21) Appl. No.: 16/316,647

(22) PCT Filed: Jul. 12, 2017

(86) PCT No.: PCT/EP2017/067604
§ 371 (c)(1),
(2) Date: Jan. 10, 2019

(87) PCT Pub. No.: WO2018/011297
PCT Pub. Date: Jan. 18, 2018

(65) Prior Publication Data
US 2019/0156951 A1    May 23, 2019

Related U.S. Application Data

(60) Provisional application No. 62/361,853, filed on Jul. 13, 2016.

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/7221* (2013.01); *A61B 5/7246* (2013.01); *G16H 50/50* (2018.01); *G16H 50/70* (2018.01)

(58) Field of Classification Search
CPC ........ G16H 50/20; G16H 50/70; G16H 50/50; A61B 5/7221; A61B 5/7246; A61B 5/7264
See application file for complete search history.

(56) References Cited

U.S. PATENT DOCUMENTS 5,215,098 A * 6/1993 Steinhaus ............ A61B 5/7232
                                                    600/515
5,706,402 A    1/1998 Bell
(Continued)

OTHER PUBLICATIONS

Chao, et al., "Blind Biosignal Classification Framework Based on DTW Algorithm", Proceedings of the International Conference on Machine Learning and Cybernetics, Guilin, Jul. 10-13, 2011, pp. 1684-1689.

*Primary Examiner* — Ryan W Sherwin (57) ABSTRACT

A central signal segregation station (100) employs a signal acquisition controller (103) and a signal segregation controller (104). In operation, the signal acquisition controller (103) receives a plurality of different types of physiological signals from a plurality of unknown physiological sensors (10; 20; 30; 40; 50; 60; 70; 80). For a monitoring of the physiological signals, the signal segregation controller (104) identifies a particular type of each physiological signal based on distinct signal features of each physiological signal corresponding to a different physiological signal model (101) among a plurality of physiological signal models (101) derived from known types of physiological sensors. For analyzing the physiological signals, the station (100) may further employ a signal analyzing controller (105) executing signal quality processing of the physiological signals, providing signal-specific feedback to any physiological sensor(s) communicating low quality physiological signal(s), annotating specific regions of each physiological signal
(Continued)

having maximum diagnostic information and/or performing a confirmatory diagnosis of the physiological signals.

20 Claims, 8 Drawing Sheets

(51) Int. Cl.
*G16H 50/70* (2018.01)
*G16H 50/50* (2018.01)

(56) References Cited

U.S. PATENT DOCUMENTS

| | | | |
|---|---|---|---|
| 6,424,960 B1 | 7/2002 | Lee et al. | |
| 6,904,269 B1* | 6/2005 | Deshpande | H04L 27/0012 |
| | | | 324/76.11 |
| 7,010,514 B2 | 3/2006 | Maekawa et al. | |
| 2005/0007091 A1 | 1/2005 | Makeig et al. | |
| 2011/0071376 A1* | 3/2011 | McKenna | G16H 40/40 |
| | | | 600/336 |
| 2013/0338519 A1 | 12/2013 | Chen et al. | |
| 2014/0372346 A1 | 12/2014 | Phillipps et al. | |
| 2016/0148375 A1* | 5/2016 | Oh | G16H 30/20 |
| | | | 382/131 |
| 2016/0151022 A1* | 6/2016 | Berlin | A61B 5/7246 |
| | | | 600/301 |
| 2016/0235374 A1* | 8/2016 | Miller | G06F 1/163 |

\* cited by examiner

CENTRAL SIGNAL SEGREGATION SYSTEM

CROSS-REFERENCE TO PRIOR APPLICATIONS

This application is the U.S. National Phase application under 35 U.S.C. § 371 of International Application No. PCT/EP2017/067604, filed on Jul. 12, 2017, which claims the benefit of U.S. Provisional Application No. 62/361,853, filed Jul. 13, 2016. These applications are hereby incorporated by reference herein, for all purposes.

TECHNICAL FIELD

Various embodiments of the present disclosure generally relate to central monitoring systems and more particularly, but not exclusively, relates to central monitoring systems for monitoring and analyzing signals representative of human physiological activity (e.g., cardiovascular, respiratory, skin physiology, etc.).

BACKGROUND

An outpatient, as used herein, is a patient who is not hospitalized overnight after visiting a healthcare facility (e.g., a hospital, a clinic, etc.) for a diagnosis and/or a treatment of an unhealthy condition. Mobile physiological sensors as known in the art of the present disclosure provide an efficient, accurate and economic method for monitoring a health of outpatients, particularly for supporting energy expedition calculations of outpatients.

Examples of such mobile physiological sensors include, but are not limited to, electrocardiogram ("ECG") monitors, respiration electrode patches, pulse oximeters, blood pressure monitors, galvanic skin response sensors, skin temperature sensors, heat flux sensors and near body temperature sensors. Future mobile physiological sensors may include, but not be limited to, arterial blood gas sensors, electroencephalography ("EEC") sensors and electromyogram ("EMG") sensors.

A central monitoring station, as the term is used herein, implements a communication protocol for exchanging information with remote sensors like mobile physiological sensors. A communication protocol standard of particular relevance in the domain of a physiological signal monitoring and analyzing by a central monitoring station is the global ISO/IEEE 11073 Personal Health Device (PHD) Communication family of standards. Current implementations of this family of standards involve the exchange of source identifying information of a mobile physiological sensor whereby a central monitoring station knows the type of physiological signal being communicated by the mobile physiological sensor. More particularly, an encrypted payload may be sent by the mobile physiological sensor across a communication channel established between the mobile physiological sensor and the central monitoring station whereby the payload includes bit information explicitly mapping the mobile physiological sensor and whereby the central monitoring station decrypts and deciphers the bit information to identify the type of physiological signal being communicated by the mobile physiological sensor. This dependency by the central monitoring station of source identifying information of the physiological sensor facilitates an applicable monitoring and analyzing of the physiological signal by the central monitoring station.

Figure 1:
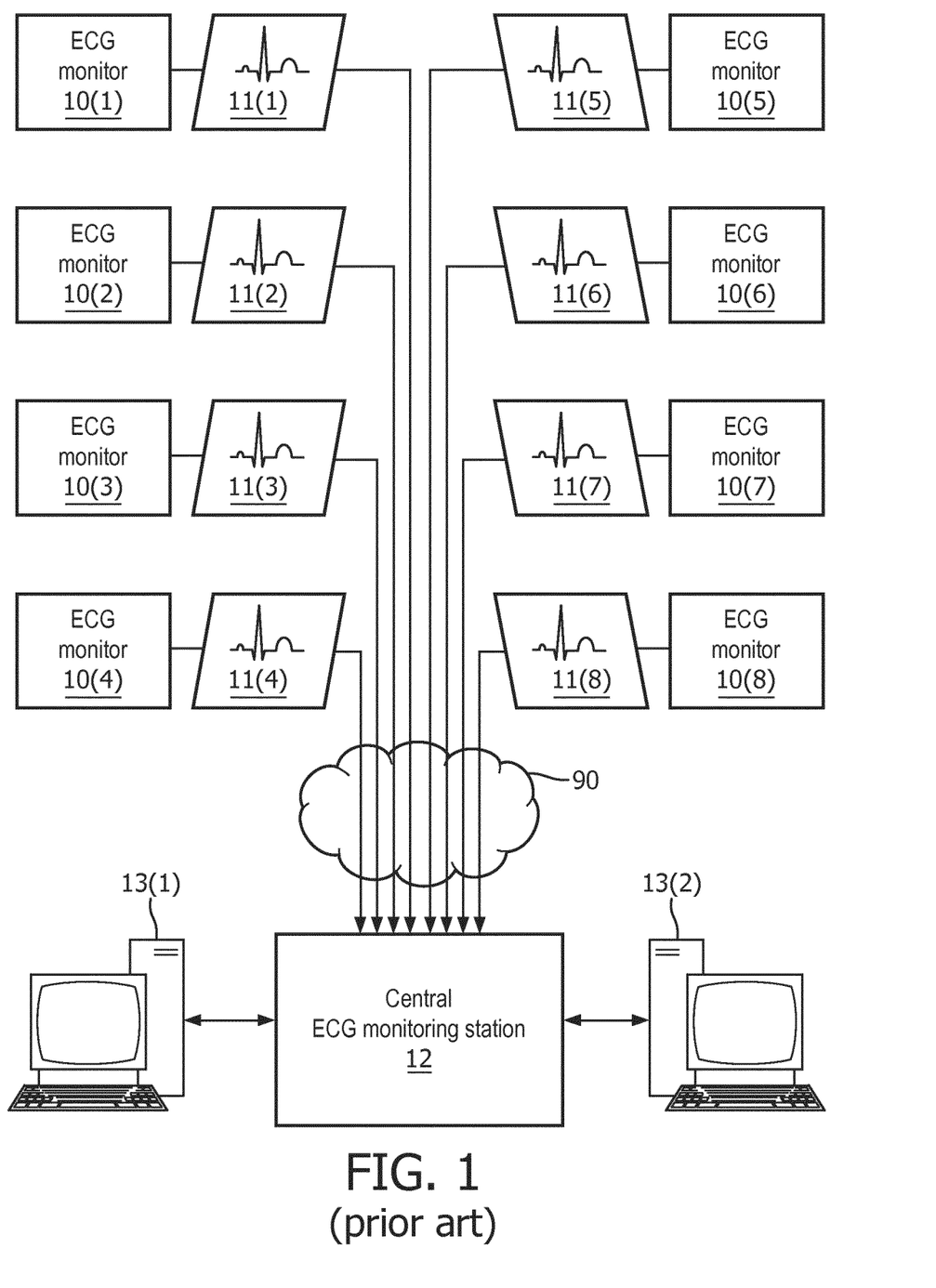
FIG. 1 illustrates an exemplary embodiment of a central ECG monitoring system as known in the art.

For example, FIG. 1 illustrates a central electrocardiogram ("ECG") monitoring station 12 for exchanging information with eight (8) ECG monitors 10. Central ECG monitoring station 12 and ECG monitors 10 implement a communication protocol (e.g., the ISO/IEEE 11073-20601 bi-directional communication protocol) involving the exchange of source identifying information of ECG monitors 10 via playoads explicitly mapping ECG monitors 10 on a protocol layer (e.g., a transport layer) to thereby prepare central ECG monitoring station 12 and ECG monitors 10 for application layer messaging of ECG signals 11 from ECG monitors 10 to station 12. This dependency by ECG central monitoring station 12 of source identifying information of ECG monitors 10 facilitates applicable monitoring and analyzing of ECG signals 11 via workstations 13 of central ECG monitoring station 12 (e.g., a normality/abnormality interpretation of ECG signals 11).

A variety in the types of mobile physiological sensors has been increasing in view of an ever increasing population of outpatient requiring long-term care due to a rising average life expectancy, a higher ratio of seniors among the general population and an increased prevalence of chorale diseases. With the increasing variety of types of mobile physiological sensors entering the healthcare market, there is a need for a central monitoring station having an independency on physiological sensor identifying information for signal monitoring and/or analysis.

SUMMARY

To improve upon the advantages and benefits of central monitoring stations for monitoring and/or analyzing one or more physiological signals, the present disclosure provides systems, stations, controllers and methods premised on an implementation of an independency of physiological sensor identifying information for signal monitoring and/or analysis of physiological signals, particularly physiological signals generated by varied types of physiological sensors.

For purposes of the present disclosure, the term "central monitoring station" broadly encompasses all central monitoring stations, known prior to the present disclosure, having a dependency on physiological sensor identifying information for monitoring and/or analyzing one or more types of physiological signals (e.g., a need for payload bit information explicitly mapping physiological sensors generated the physiological signals). Examples of such central monitoring stations include, but are not limited to, the IntelliVue Information Center iX (PIIC).

Also for purposes of the present disclosure, the term "central signal segregation station" broadly encompasses a central monitoring station having a structural configuration incorporating inventive principles of the present disclosure as exemplary described herein for implementing an independency of physiological sensor identifying information for signal monitoring and/or analysis of a plurality of physiological signals, particularly physiological signals generated by varied types of physiological sensors, and the term "central signal segregation method" broadly encompasses all methods that incorporate the inventive principles of the present disclosure as exemplary described herein for implementing an independency of physiological sensor identifying information for signal monitoring and/or analysis of physiological signals by a central signal segregation station.

Various embodiments described herein include a central signal segregation station employing a signal acquisition controller and a signal segregation controller. In operation, the signal acquisition controller receives a plurality of different types of physiological signals from a plurality of unknown physiological sensors (e.g., electrocardiogram ("ECG") monitors, respiration electrode patches, pulse oximeters, blood pressure monitors, galvanic skin response sensors, skin temperature sensors, heat flux sensors and near body temperature sensors).

For a monitoring of the physiological signals, the signal segregation controller identifies a particular type of each physiological signal based on distinct signal features of each physiological signal corresponding to a different physiological signal model among a plurality of physiological signal models derived from known types of physiological sensors. The distinct signal features of each physiological signal established an independency by the signal segregation controller of physiological sensor identifying information for signal monitoring and/or analysis of the physiological signals (e.g., the signal segregation controller identifies each physiological signal without any assistance or need for payload bit information explicitly mapping physiological sensors generated the physiological signals).

For an analysis of the identified physiological signals with or without monitoring, the central signal segregation station may further employ a signal analyzing controller. If employed, subsequent to the type identification of each physiological signal by the signal segregation controller, the signal analyzing controller may further:

(1) execute signal quality processing of the physiological signals (e.g., a signal-to-noise quality measurement);

(2) provide signal-specific feedback to any physiological sensor(s) communicating low quality physiological signal(s);

(3) annotate specific regions of each high quality physiological signal having maximum diagnostic information; and/or (4) perform an auto confirmatory diagnosis of each high quality physiological signal, particularly in view of context aware information appended to a physiological signal (e.g., a geolocation and any accelerated motion of a physiological sensor).

Various embodiments described herein include a central signal segregation system employing a plurality of unknown physiological sensors and a central signal segregation station. In operation, each unknown physiological sensor transmits a different type of physiological signals to the central signal segregation station (e.g., electrocardiogram ("ECG") signal, a respiration signal $1/\Omega_R$, an oxygen saturation signal $SO_2$, a blood pressure signal (systolic/diastolic), a galvanic skin response signal $1/\Omega_S$, a skin temperature signal $°F./°C.$, a heat flux signal $W/m^2$ and a near body temperature signal $°F./°C.$).

For a monitoring of the physiological signals, the central signal segregation station identifies a particular type of each physiological signal based on distinct signal features of each physiological signal corresponding to a different physiological signal model among a plurality of physiological signal models derived from known types of physiological sensors. The distinct signal features of each physiological signal established an independency by the signal segregation controller of physiological sensor identifying information for signal monitoring and/or analysis of the physiological signals (e.g., the signal segregation controller identifies each physiological signal without any assistance or need for payload bit information explicitly mapping physiological sensors generated the physiological signals).

For an analysis of the identified physiological signals with or without monitoring, the central signal segregation station may further:

(1) execute signal quality processing of the physiological signals (e.g., a signal-to-noise quality measurement);

(2) provide signal-specific feedback to any physiological sensor(s) communicating low quality physiological signal(s);

(3) annotate specific regions of each high quality physiological signal having maximum diagnostic information; and/or (4) perform a confirmatory diagnosis of each high quality physiological signals particularly in view of context aware information appended to a physiological signal (e.g., a geolocation and any accelerated motion of a physiological sensor).

Various embodiments described herein include a central signal segregation method involving a central signal segregation station receiving a plurality of different types of physiological signals from a plurality of unknown physiological sensors (e.g., electrocardiogram ("ECG") monitors, respiration electrode patches, pulse oximeters, blood pressure monitors, galvanic skin response sensors, skin temperature sensors, heat flux sensors and near body temperature sensors).

For a monitoring of the physiological signals, the central signal segregation method further involves the central signal segregation station identifying the type of each physiological signal based on distinct signal features of each physiological signal corresponding to a different physiological signal model among a plurality of physiological signal models derived from known types of physiological sensors. The distinct signal features of each physiological signal established an independency by the signal segregation controller of physiological sensor identifying information for signal monitoring and/or analysis of the physiological signals (e.g., the signal segregation controller identifies each physiological signal without any assistance or need for payload bit information explicitly mapping physiological sensors generated the physiological signals).

For an analysis of the identified physiological signals with or without monitoring, the central signal segregation method may further involve the central signal segregation station:

(1) executing signal quality processing of the physiological signals (e.g., a signal-to-noise quality measurement);

(2) providing signal-specific feedback to any physiological sensor(s) communicating low quality physiological signal(s);

(3) annotating specific regions of each high quality physiological signal having maximum diagnostic information; and/or (4) performing a confirmatory diagnosis of each high quality physiological signal, particularly in view of context aware information appended to the physiological signal (e.g., a geolocation and any accelerated motion of a physiological sensor).

For purposes of the present disclosure, (1) terms of the art including, but not limited to, "physiological sensor", "monitoring", "analyzing" and "diagnosing" are to be interpreted as understood in the art of the present disclosure and as exemplary described herein;

(2) the phrase "unknown physiological sensors" broadly encompasses mobile and immobile physiological sensors excluding source identifying information within a communication protocol implemented by the physiological sensors;

(3) the term "physiological signal model" broadly encompasses all models for estimating a probability of a particular type of a physiological signal based on one or more signal features of the physiological signal. An example of a physiological signal model includes machine learning methods (e.g., supervised, unsupervised and semi-supervised), but is not limited to, a logistic regression model, a linear regression model, a support vector machine model, a classification model, a clustering model, a dimensionality reduction model, an association rule learning model and a decision tree model;

(4) the term "signal features" broadly encompasses any and all distinctive features of a physiological signal facilitating an identification of the physiological signal. Examples of such signal features include, but are not limited to:
(a) a resistive index;
(b) a pulsatility index;
(c) a relative acceleration time;
(d) a relative decay time;
(e) a flow acceleration;
(f) a constant flow ratio;
(g) a height width index;
(h) a peak to peak pulsatility index;
(i) a bandwidth index;
(j) an envelope roll-off;
(k) a higher order statistics;
(l) an envelope centroid;
(m) an average rising slope;
(n) a spectral broadening ratio; and
(o) a profile shape;

(5) the term "low quality" broadly encompasses any qualitative nature of a physiological signal impeding an analysis of the physiological signal, and the term "high quality" broadly encompasses a qualitative nature of a physiological signal suitable for an analysis of the physiological signal;

(6) the term "context aware information" broadly encompasses any information related to an operational and environment context within which a physiological sensor is generating a physiological signal. Examples of context aware information include, but are not limited to, a geolocation, a temperature, a light flux, a noise level and an accelerated motion of a physiological sensor.

(7) the term "controller" broadly encompasses all structural configurations of an application specific main board or an application specific integrated circuit housed within or linked to a central signal segregation station for controlling an application of various inventive principles of the present disclosure as subsequently described herein. The structural configuration of the controller may include, but is not limited to, processor(s), computer-usable/computer readable storage medium(s), an operating system, application module(s), peripheral device controller(s), slot(s) and port(s). Any descriptive labeling of a controller herein (e.g., "signal acquisition", and "signal segregation") serves to identify a controller as described and claimed herein without specifying or implying any additional limitation to the term "controller";

(8) the term "application module" broadly encompasses a component of a controller consisting of an electronic circuit and/or an executable program (e.g., executable software and/or firmware stored on non-transitory computer readable medium(s)) for executing a specific application. Any descriptive labeling of an application module herein (e.g., a "signal acquisition module", "signal source identifier", "signal quality manager", "annotation manager", "diagnostic analyzer" and "database manager") serves to identify a particular application module as described and claimed herein without specifying or implying any additional limitation to the term "application module"; and (9) the terms "signal" and "data" broadly encompasses all forms of a detectable physical quantity or impulse (e.g., voltage, current, etc.) as understood in the art of the present disclosure and as exemplary described herein for transmitting information in support of applying various inventive principles of the present disclosure as subsequently described herein. Any descriptive labeling for the terms "signal" and "data" herein facilitates a distinction between signals as described and claimed herein without specifying or implying any additional limitation to the terms "signal" and "data".

The foregoing forms and other forms of the inventions of the present disclosure as well as various features and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the present inventions of the present disclosure being defined by the appended claims and equivalents thereof.

DETAILED DESCRIPTION

Figure 2:
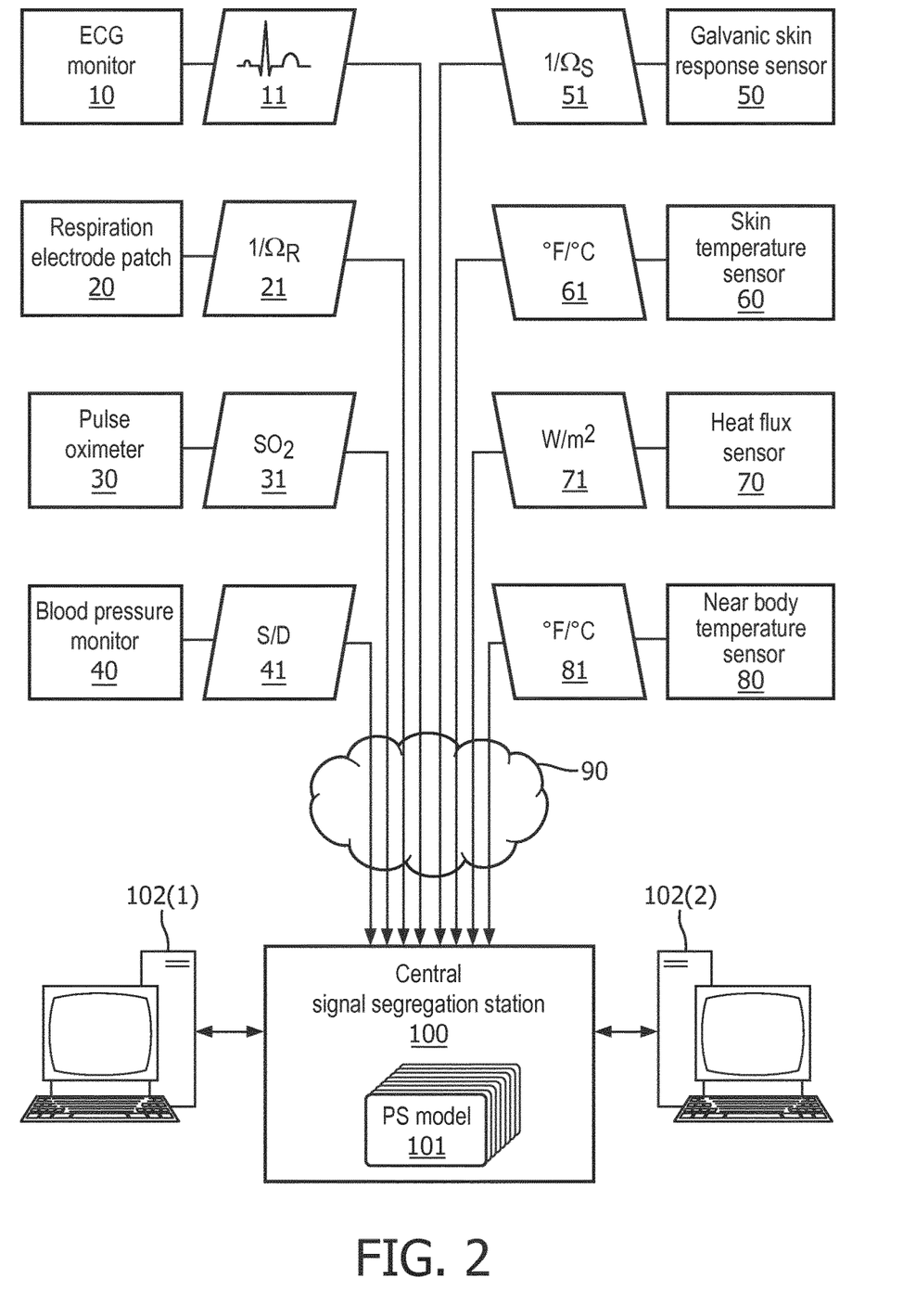
FIG. 2 illustrates an exemplary embodiment of a central signal segregation system in accordance with the inventive principles of the present disclosure.
Figure 3:
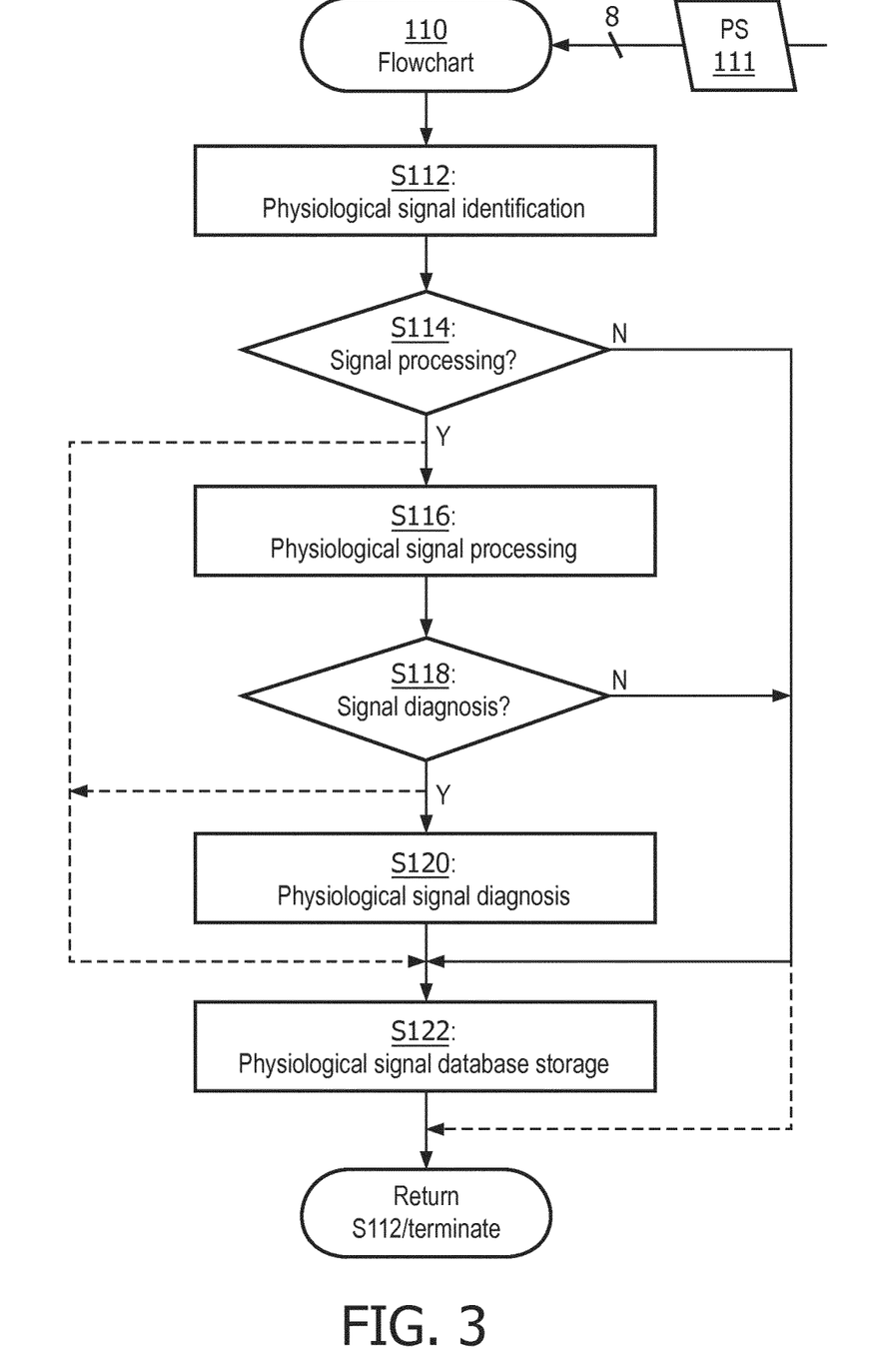
FIG. 3 illustrates a flowchart representative of an exemplary embodiment of a central signal segregation method in accordance with the inventive principles of the present disclosure.

To facilitate an understanding of the embodiments of the present disclosure, the following description of FIGS. 2 and 3 teaches inventive principles of central signal segregation systems and central signal segregation methods of the present disclosure. While the description of FIGS. 2 and 3 are provided in the context of a plurality of mobile physiological sensors including an electrocardiogram ("ECG") monitor, a respiration electrode patch, a pulse oximeter, a blood pressure monitor, a galvanic skin response sensor, a skin temperature sensor, a heat flux sensor and a near body temperature sensor, those having ordinary skill in the art of the present disclosure will appreciate how to apply the inventive principles of the present disclosure to make and use a variety of central signal segregation systems and central signal segregation methods of the present disclosure in the context of numerous physiological sensors as shown and of additional physiological sensors, mobile and/or immobile.

Referring to FIG. 2, one embodiment of a central signal segregation system of the present disclosure employs, as known in the art of the present disclosure, a plurality of physiological sensors including:

1. an ECG monitor 10 generating an ECG signal 11;
2. a respiration electrode patch 20 generating a respiration signal 21;
3. a pulse oximeter 30 generating an oxygen saturation signal 31;
4. a blood pressure monitor generating a blood pressure signal 41;
5. a galvanic skin response sensor 50 generating a galvanic skin response signal 51;
6. a skin temperature sensor 60 generating a skin temperature signal 61;
7. a heat flux sensor 70 generating a heat flux signal 71, and
8. a near body temperature sensor 80 generating a near body temperature signal 81.

Still referring to FIG. 2, the physiological sensors transmit the physiological signals via a network 90 (e.g., an intranet or an internet) to a central signal segregation station 100 as shown. As will be understood, the central signal segregation station may be implemented in various hardware arrangements such as a stand-alone server or as one or more virtual machines hosted on hardware in a cloud computing environment or distributed among multiple cloud computing environments. In practice, the physiological sensors may be sequentially or concurrently transmitting a subset or an entire set of the physiological signals, and two or more of the physiological sensors may be monitoring the same individual outpatient.

Also in practice, the physiological sensors and central signal segregation station 100 implement a communication protocol (e.g., the ISO/IEEE 11073-20601 bi-directional communication protocol) excluding the exchange of source identifying information of the physiological sensors of any layer of the communication protocol (e.g., excluding payload bit information explicitly mapping physiological sensors generated the physiological signals). To address this independency by central signal segregation station 100 of source identifying information of the "unknown" physiological sensors, central signal segregation station 100 identifies a particular type of each physiological signal based on distinct signal features of each physiological signal corresponding to a different physiological signal model among a plurality of physiological signal models 101 derived from the known types of the physiological sensors.

Physiological signal models 101 provide for an estimation of a probability of a particular type of a physiological signal based on one or more signal features of the physiological signal as will be further described herein. In the context of the unknown physiological sensors of FIG. 2, central signal segregation station 100 is trained to generate:

1. an ECG signal model derived from signal features of training ECG signals generated by numerous and/or various types of ECG monitors whereby the ECG signal model provides an estimation of a probability that any physiological signal received by central signal segregation station 100 is an ECG signal;
2. a respiration signal model derived from signal features of training respiration signals generated by numerous and/or various types of respiration electrode patches whereby the respiration signal model provides an estimation of a probability that any physiological signal received by central signal segregation station 100 is a respiration signal;
3. an oxygen saturation signal model derived from signal features of training oxygen saturation signals generated by numerous and/or various types of pulse oximeters whereby the oxygen saturation signal model provides an estimation of a probability that any physiological signal received by central signal segregation station 100 is an oxygen saturation signal;
4. a blood pressure signal model derived from signal features of training blood pressure signals generated by numerous and/or various types of blood press monitors whereby the blood pressure signal model provides an estimation of a probability that any physiological signal received by central signal segregation station 100 is a blood pressure signal;
5. a galvanic skin response signal model derived from signal features of training galvanic skin response signals generated by numerous and/or various types of galvanic skin response sensors whereby the galvanic skin response signal model provides an estimation of a probability that any physiological signal received by central signal segregation station 100 is a galvanic skin response signal;
6. a skin temperature signal model derived from signal features of training skin temperature signals generated by numerous and/or various types of skin temperature sensors whereby the skin temperature signal model provides an estimation of a probability that any physiological signal received by central signal segregation station 100 is a skin temperature signal;
7. a heat flux signal model derived from signal features of training heat flux signals generated by numerous and/or various types of heat flux sensors whereby the heat flux signal model provides an estimation of a probability that any physiological signal received by central signal segregation station 100 is a heat flux signal; and
8. a near body temperature signal model derived from signal features of training near body temperature signals generated by numerous and/or various types of near body temperature sensors whereby the near body temperature signal model provides an estimation of a probability that any physiological signal received by central signal segregation station 100 is a near body temperature signal.

From the type identification of the physiological signals, central signal segregation station 100 process the physiological signals via the application layers of the communication protocol and operators of central signal segregation station 100 may access monitoring application(s) via workstations 102 to thereby visually monitor the physiological signals.

Additionally, central signal segregation station 100 may execute analyzing application(s) that provide analytical information to the operators via workstations 102 and/or as feedback to the physiological sensors as will be further described herein.

Also, context aware information may be appended by the physiological sensors to the physiological signals in support of the analyzing application(s) of central signal segregation station 100 as will be further described herein.

More particularly, FIG. 3 illustrates a flowchart 110 representative of one embodiment of a central signal segregation method of the present disclosure executable by central signal segregation station 100 (FIG. 2).

Referring to FIGS. 2 and 3, central signal segregation station 100 executes flowchart 110 in responsive to a concurrent reception of physiological signals 111 from the unknown physiological sensors.

Specifically, a stage S112 of flowchart 110 encompasses central signal segregation station 100 identifying a particular type of each physiological signal based on distinct signal features of each physiological signal corresponding to a particular physiological signal model among a plurality of physiological signal models 101 derived from the known types of the physiological sensors.

Upon completion of stage S112, if central signal segregation station 100 is not structurally configured for signal quality processing of the identified physiological signals (e.g., a signal-to-noise quality measurement), then central signal segregation station 100 proceeds to a stage S122 of flowchart 110 to manage a stream storage of the physiological signals within a database for monitoring purposes.

Otherwise, if central signal segregation station 100 is structurally configured for signal quality processing of the identified physiological signals (e.g., a signal-to-noise quality measurement), then central signal segregation station 100 proceeds to a stage S116 of flowchart 110 to execute signal quality processing of the identified physiological signals and provide signal-specific feedback to any physiological sensor(s) communicating low quality physiological signal(s) as will be further described herein.

Prior to proceeding to stage S116, central signal segregation station 100 may initiate stage S122 for a stream storage of the physiological signals within a database as symbolized by the dashed arrows for monitoring purposes.

Upon completion of stage S116, if central signal segregation station 100 is not structurally configured for signal-specific diagnostic analyzing of the identified physiological signals of high quality, then central signal segregation station 100 proceeds to stage S122 of flowchart 110 to manage a stream storage of the physiological signals within the database.

Otherwise, if central signal segregation station 100 is structurally configured for signal-specific diagnostic analyzing of the identified physiological signals of high quality, then central signal segregation station 100 proceeds to a stage S120 of flowchart 110 to annotate specific regions of each identified physiological signal of high quality having maximum diagnostic information, and/or to perform a confirmatory diagnosis of identified physiological signal of high quality, particularly in view of context aware information appended to the physiological signals (e.g., a geolocation and any accelerated motion of a physiological sensor) as will be further described herein.

Prior to proceeding to stage S120, central signal segregation station 100 may initiate or continue stage S122 for a stream storage of the physiological signals and associated processing information within the database as symbolized by the dashed arrows for monitoring and analytical purposes.

Upon completion of stage S120, central signal segregation station 100 may initiate or continue stage S122 for a stream storage of the physiological signals and associated processing and diagnostic information within the database for monitoring and analytical purposes.

Flowchart 110 is executed by central signal segregation station 100 in sequential or overlapping cycles. Thus, at any time during flowchart 110 or upon completion of stage S122, central signal segregation station 100 returns to stage S112 to initiate a new cycle until such time flowchart 110 is terminated (e.g., central signal segregation station 100 is powered down for maintenance and/or upgrade).

From the descriptions of FIGS. 2 and 3, those having ordinary skill in the art of the present disclosure will appreciate the implementation by central signal segregation station 100 (FIG. 2) and flowchart 110 (FIG. 3) of an independency of physiological sensor identifying information for signal monitoring and optional analysis of the physiological signals.

To facilitate a further understanding of the present disclosure, the following description of FIGS. 4-9 further teaches inventive principles of central signal segregation stations of the present disclosure. While the description of FIGS. 4-9 are provided in the context of the plurality of mobile physiological sensors shown in FIG. 2, those having ordinary skill in the art of the present disclosure will appreciate how to apply the inventive principles of the present disclosure to make and use a variety of central signal segregation stations of the present disclosure in the context of numerous physiological sensors as shown in FIG. 2 and of additional physiological sensors, mobile and/or immobile.

Figure 4:
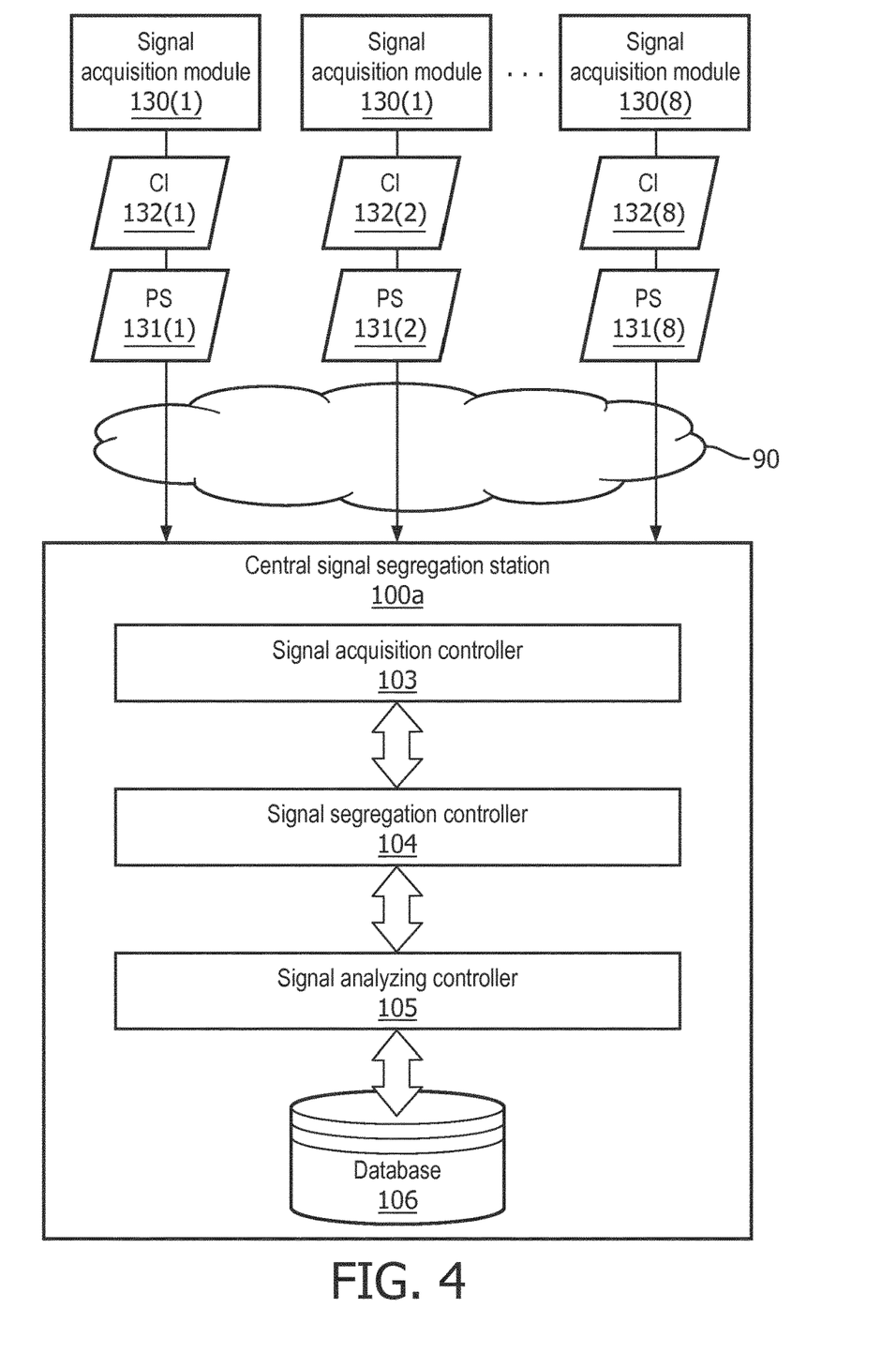
FIG. 4 illustrate an exemplary embodiment of a central signal segregation station in accordance with the inventive principles of the present disclosure.

Referring to FIG. 4, a signal acquisition module 130 of the present disclosure is installed on each unknown physiological sensor and structurally configured to transmit an associated physiological signal 131 in accordance with a communication protocol exclusive of any physiological sensor identifying information. If an associated physiological sensor in practice incorporates devices for generating context aware information 132 (e.g., geolocation and accelerated motion of the physiological sensor), then a signal acquisition module 130 will append the context aware information 132 with the physiological signal 131. Alternatively, context aware information 132 may be derived from a mobile phone or any connected device to the subject.

Still referring to FIG. 4, an embodiment 100a of central signal segregation station 100 (FIG. 2) employs a signal acquisition controller 103, a signal segregation controller 104, a signal analyzing controller 105, and a database 106. In practice, controllers 103-105 may be segregated as shown, or partially or fully integrated. Also, in practice, database 106 may be segregated from controllers 103-105 as shown or integrated/distributed within one or more of controllers 103-105.

Signal acquisition controller 103 is structurally configured for receiving physiological signals 131 in accordance with the communication protocol exclusive of any physiological sensor identifying information (e.g., excluding any payload bit information explicitly mapping the associated physiologic sensor). In practice, signal acquisition controller 103 controls transmitters, receivers and/or transceivers (not shown) of central signal segregation station 100 as known in the art for receiving physiological signals 131 in accordance with the communication protocol and provides physiological signals 131 to signal segregation controller 104.

Signal segregation controller 104 is structurally configured in accordance with the inventive principles of the present disclosure for executing stage 112 of flowchart 110 (FIG. 3) and for executing stage S122 of flowchart 110 (if applicable). In practice, signal segregation controller 104 is trained to generate physiological signal models 101 as previously described herein (FIG. 2) and to apply each received physiological signal 131 to each physiological signal model 101 to identify a particular type of each physiological signal 131.

In practice, any embodiment of signal segregation controller 104 will be dependent upon various operational factors as will be appreciated by those having ordinary skill in the art of the present disclosure including, but not limited to, a variance in the types of physiological signals to be monitored and/or analyzed.

Figure 5A:
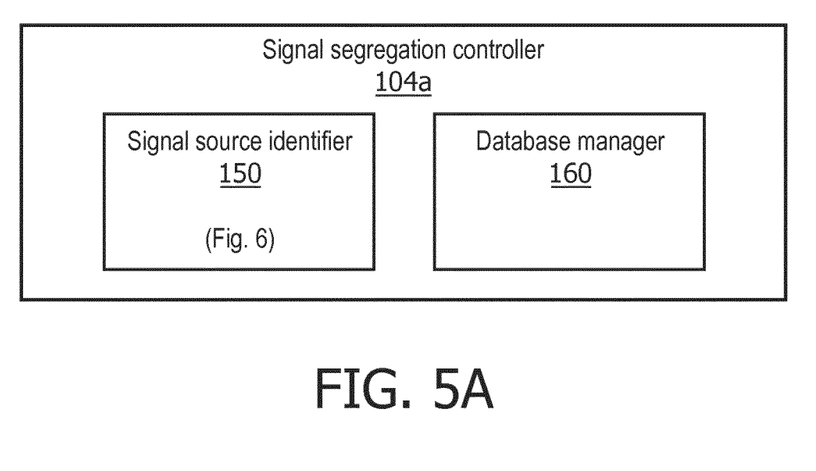
FIG. 5A illustrates an exemplary embodiment of a signal segregation controller in accordance with the inventive principles of the present disclosure.

Referring to FIG. 5A, one embodiment 104a of signal segregation controller 104 employs a signal source identifier 150 and a database manager 160.

Signal source identifier 150 is structurally configured in accordance with the inventive principles of the present disclosure to generate the physiological signal models 101 (FIG. 2) for an estimation of a probability of a particular type of each physiological signal 131 based on one or more signal features of physiological signal 131. In practice, signal source identifier 150 may generate physiological signal models in the form of a logistic regression model, a linear support vector machine model and/or a decision tree model involving an extraction of signal features including, but not limited to:

1. a resistive index;
2. a pulsatility index;
3. a relative acceleration time;
4. a relative decay time;
5. a flow acceleration;
6. a constant flow ratio;
7. a height width index;
8. a peak to peak pulsatility index;
9. a bandwidth index;
10. an envelope roll-off;
11. a higher order statistics;
12. an envelope centroid;
13. an average rising slope;
14. a spectral broadening ratio; and
15. a profile shape.

Figure 6A:
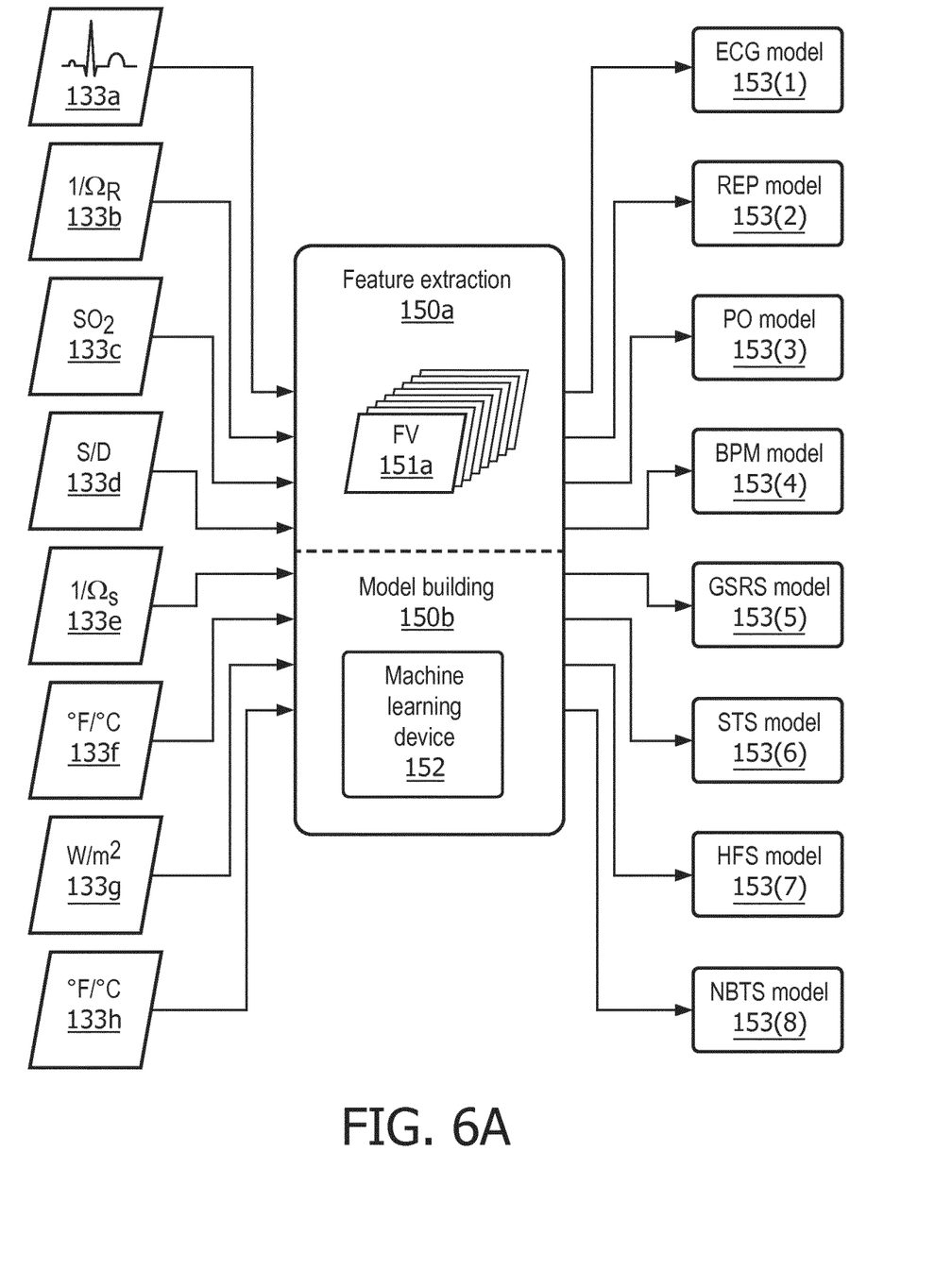
FIGS. 6A and 6B illustrate an exemplary embodiment of a signal source identifier in accordance with the inventive principles of the present disclosure.

For example, in a training phase of signal source identifier 150, FIG. 6A illustrate a feature extraction 150a by signal source identifier 150 of training physiological signals 133a-133h in the form of feature vectors 151 being an n-dimensional vector of signal features (s), n≥1 or a vector loop. Signal source identifier 50 thereafter applies a machined learning device 152 (e.g., a support vector machine) to each feature vector 151 for model building 150b of physiological signal models 153 whereby the signal features of a feature vector 151 serve as independent variables of models 153 and the dependent variable provides a probability estimation of the corresponding training physiological signal 133.

Figure 6B:
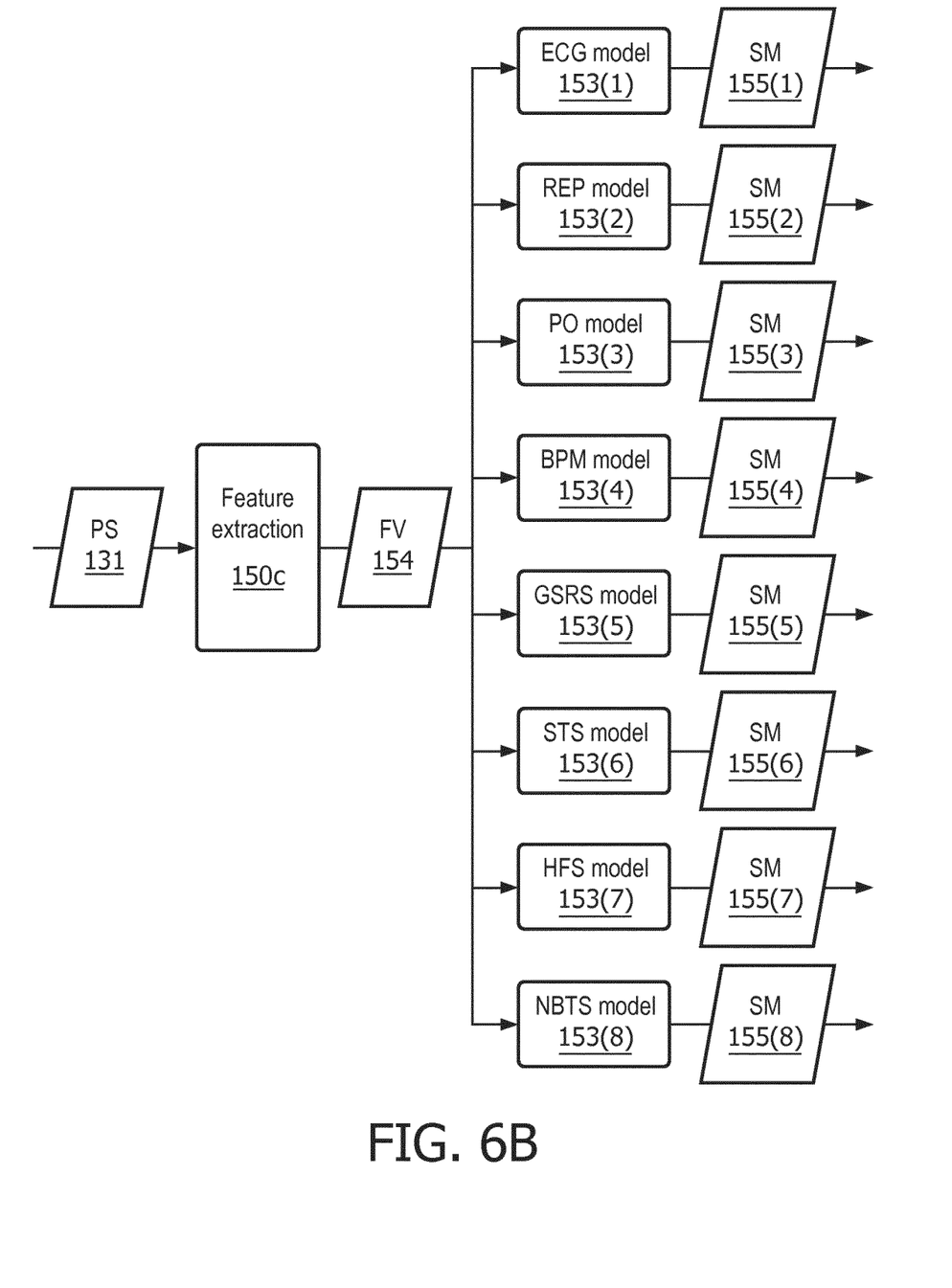

By further example, in an identification phase of signal source identifier 150, FIG. 6B illustrate a feature extraction 150c by signal source identifier 150 of received physiological signals 133 in the form of a feature vector 154 being an n-dimensional vector of signal features(s), n≥1 or a vector loop. Signal source identifier 50 thereafter applies feature vector 154 to each physiological signal model 153 to obtain a similarity measurement 155 (e.g., 0≤SM≤1). Physiological signal 131 is deemed to correspond the physiological signal model 153 providing the higher similarity measurement 155. For example, upon sufficient training, if physiological signal 131 is an ECG signal, then similarity measurement 155(1) of ECG model 153(1) should have the highest similarity measurement among all similarity measurements 151.

Referring back to FIG. 4, signal analyzing controller 105 is structurally configured in accordance with the inventive principles of the present disclosure for executing stages S116-S122 of flowchart 110 (FIG. 3). In practice, signal analyzing controller 105 executes analyzing application(s) that provide analytical information and/or signal feedback to the user(s)/monitor(s) of the physiological sensor(s) and/or operator(s) of the central signal segregation station will be further described herein.

In practice, any embodiment of signal analyzing controller 105 will be dependent upon various operational factors as will be appreciated by those having ordinary skill in the art of the present disclosure including, but not limited to, any and all delineated analytical techniques to be applied to the physiological signals.

Figure 5B:
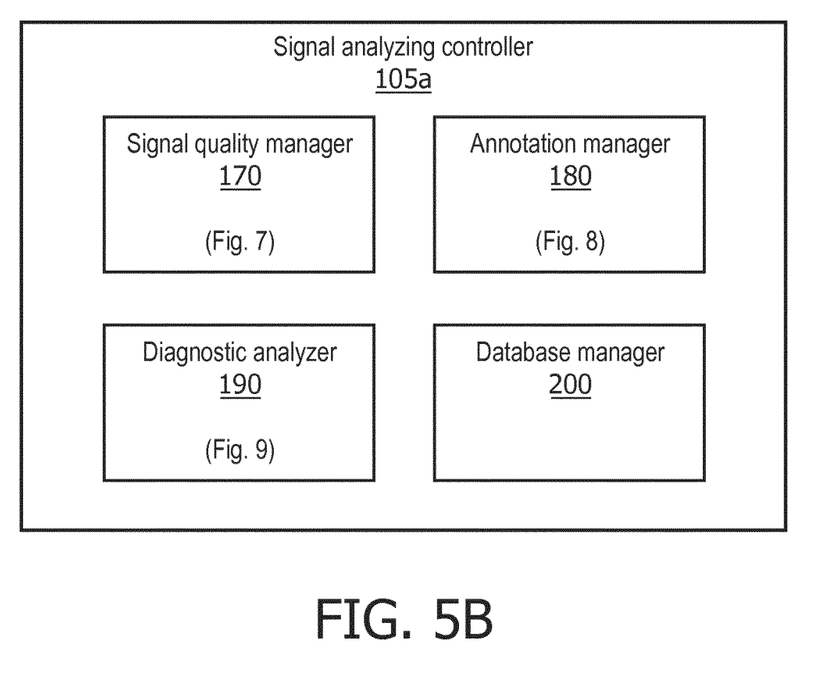
FIG. 5B illustrates an exemplary embodiment of a signal analyzing controller in accordance with the inventive principles of the present disclosure.

Referring to FIG. 5B, one embodiment 105a of signal analyzing controller 105 employs a signal quality manager 170, an annotation manager 180, a diagnostic analyzer 190 and a database manager 200.

Signal quality manager 160 is structurally configured to execute signal quality processing of the identified physiological signals and provides signal-specific feedback to any physiological sensor(s) communicating low quality physiological signal(s). In practice, signal quality manager 160 may detect a required signal-to-noise (SNR) for each identified physiological signal. Further, signal quality manager 160 may ascertain if all the relevant fiducial points, which are needed for diagnosis level prediction, are present in each identified physiological signal. Also, if the signal quality is poor, then signal quality manager 160 tries to identify the source of degradation either due to, for example, a wrong placement, an electromagnetic interference and/or a device malfunctioning of the associated physiological sensor. Signal quality manager 160 provides the feedback to a user/monitor of the physiological sensor and/or an operator of central signal segregation station on the proper usage of the device/modification within the device parameter for obtaining proper SNR.

Figure 7:
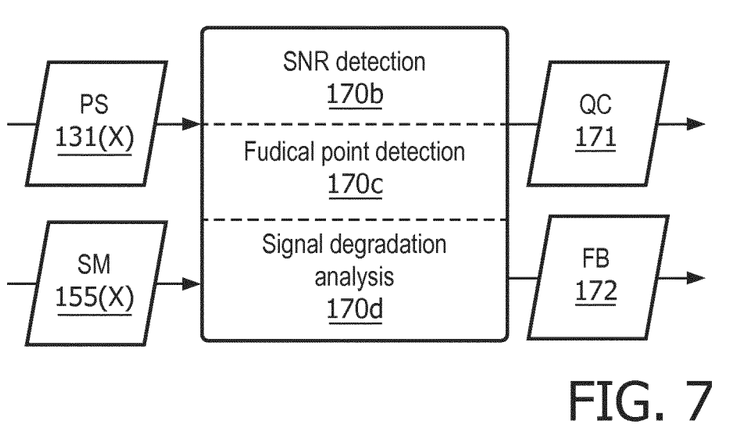
FIG. 7 illustrates an exemplary embodiment of a signal quality manager in accordance with the inventive principles of the present disclosure.

For example, as shown with a data flow in FIG. 7, signal quality manager 160 executes a signal quality processing of a physiological signal 131 based on the associated similarly measurement 155 or other signal identifier to yield a high quality check 171 or a low quality feedback 172 for database storage. Examples of the signal quality processing include, but are not limited to, a signal-to-noise quality measurement 170b and a fiducial point detection 170c. If physiological signal 131 exhibits low quality (e.g. high signal-to-noise ratio, failure to detect fiducials, etc.), then signal quality manager 170 executes a signal degradation analysis 170d involving a communication of low quality feedback signal 172 informative of the low quality nature of the physiological signal 131 with or without an identification of a determined reason for the signal degradation.

Referring back to FIG. 5B, annotation manager 180 is structurally configured to annotate specific regions of each identified high quality physiological signal having maximum diagnostic information. In practice, after an identified physiological signal has been denoted as have appreciable quality by signal quality manager 170, annotation manager 180 identifies the relevant part of the signal for analysis.

More particularly, the present disclosure recognizes that continuous monitoring of a physiological signal provides repeated signal trends which typically may or may not have any significant diagnostic value. For example, for an ECG signal, when the trend is continuously monitored, the change in ST segment, or the periodic shift of fiducial locations are of primary importance for the analysis rather than entire signal. Annotation manager 180 therefore identifies the signal regions which are unique and carry potential information for the analysis using information gain and modelling approach. Also, if content information is received (e.g., geolocation and any accelerated motion), annotation manager 80 further annotates the activity being performed during the signal acquisition with the diagnostic region(s).

Figure 8:
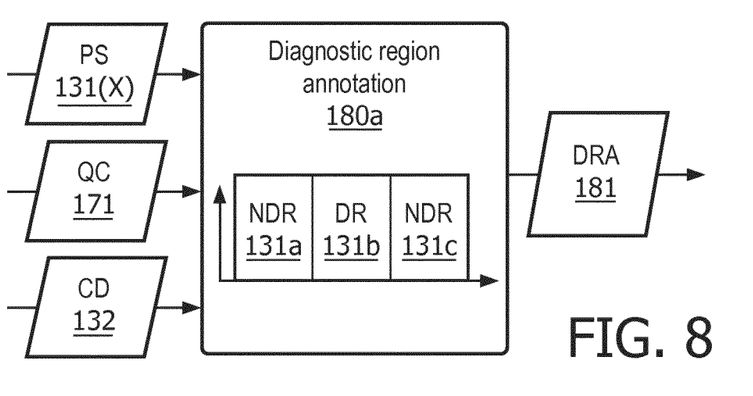
FIG. 8 illustrates an exemplary embodiment of an annotation manager in accordance with the inventive principles of the present disclosure.

For example, as shown in FIG. 8, if a quality check 171 is received for a physiological signal 131, annotation manager 180 executes a diagnostic region annotation 180a involving a delineation of diagnostic region(s) (e.g., diagnostic region 131b) and non-diagnostic region(s) (e.g., non-diagnostic regions 131a and 131c) of physiological signal 130 of a signal cycle. The exemplary diagnostic region 131b may be identified based on historical understanding of a diagnostic nature of physiological signal 131 and/or the predictive elements of the associated physiologic signal model. Annotation manager 181 generates a diagnostic region annotation 181 for database storage appended with, if applicable, content aware information 132 occurring during a diagnostic region 131b.

Referring back to FIG. 5B, diagnostic analyzer 190 is structurally configured to perform a diagnosis of an identified high quality physiological signal of based on the associated diagnostic region annotation(s), particularly in view of any context aware information appended to diagnostic region annotation(s). In practice, after an annotation of an identified high quality physiological signal, diagnostic analyzer 190 extracts a trend among the physiological signals to correlate an observation to auto diagnose any pertinent aliments whereby a personalized care plan may be pushed to a user/monitor of the physiological device and/or an operator of the central signal segregation station.

Figure 9:
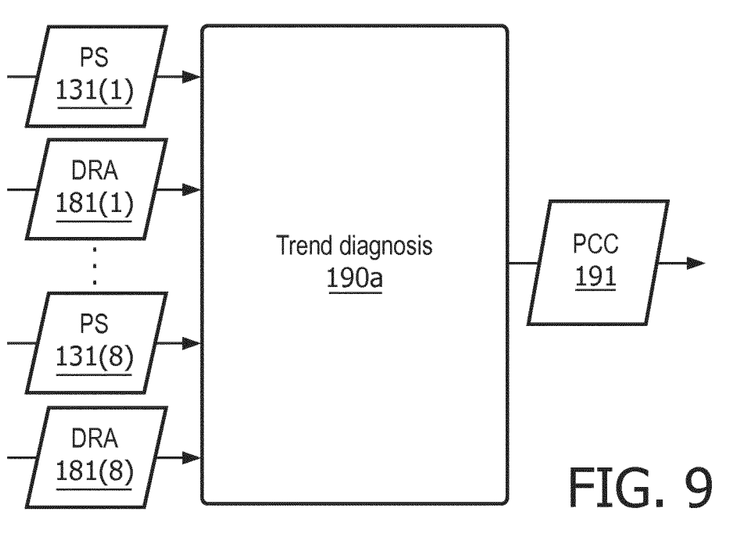
FIG. 9 illustrates an exemplary embodiment of a diagnostic analyzer in accordance with the inventive principles of the present disclosure.

For example, as shown in FIG. 9, diagnostic analyzer 190 executes a trend diagnosis 190a of physiological signals 131 from an individual subject based on the associated diagnostic region annotations 181. Any trend identification will be informative of any pertinent aliments and diagnostic analyzer 190 within the context aware information whereby a personalize care plan (PCC) may be communicated to a user/monitor of the physiological device and/or an operator of the central signal segregation station.

Referring to FIGS. 2-9, those having ordinary skill in the art will appreciate numerous benefits of the various embodiments of the present disclosure including, but not limited to, an independency of physiological sensor identifying information for signal monitoring and/or analysis of physiological signals by central signal segregation stations and methods.

Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process. Further, the term "processor" will be understood to encompass various types of hardware such as microprocessors, field-programmable gate arrays (FPGAs), application-specific integrated circuits (ASICs), and other hardware capable of performing the functions described herein. Further, as used herein, the term "non-transitory medium" will be understood to encompass both volatile memories (e.g., DRAM, SRAM, etc.) and nonvolatile memories (e.g., flash, magnetic, and optical storage) but to exclude transitory signals.

Moreover, all statements herein reciting principles, aspects, and embodiments, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles described herein. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive central signal segregation stations, controllers and methods, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A central signal segregation station, comprising:
a signal acquisition controller configured to receive a plurality of different physiological signals of unknown signal types from a plurality of physiological sensors providing unknown signal types, respectively; and
a signal segregation controller in communication with the signal acquisition controller,
   wherein, responsive to the signal acquisition controller receiving the plurality of physiological signals, the signal segregation controller is configured to control an identification of a particular type of each physiological signal, wherein the identification of the particular type of each physiological signal comprises extracting a feature vector from the physiological signal, applying the feature vector to a plurality of physiological signal models derived from physiological sensors of known signal types to obtain a similarity measurement for each physiological signal model, choosing the physiological signal model providing a highest similarity measurement.

2. The central signal segregation station of claim 1, further comprising:
a signal analyzing controller in communication with the signal segregation controller,
   wherein the signal analyzing controller is configured to control an execution of a signal quality processing of each physiological signal based on the similarity measurement of the physiological signal, wherein the signal quality processing comprises a signal-to-noise quality measurement and/or a fiducial point detection.

3. The central signal segregation station of claim 2,
wherein the signal analyzing controller is further configured to control a communication to an associated physiological sensor of the plurality of physiological sensors of a signal quality of the physiological signal.

4. The central signal segregation station of claim 1, further comprising:
a signal analyzing controller in communication with the signal segregation controller,
   wherein the signal analyzing controller is configured to annotate at least one region of each physiological signal identified by the signal segregation controller, wherein the annotating comprises delineating at least one diagnostic region and at least one non-diagnostic region and generating an annotation of the at least one diagnostic region.

5. The central signal segregation station of claim 4,
wherein the signal analyzing controller is further configured to control a communication of a personalized care plan to an associated physiological sensor of the plurality of physiological sensors fore each physiological signal, and
wherein the personalized care plan is derived from a trend diagnosis of physiological signals based on the annotations of the least one region of each physiological signal.

6. The central signal segregation station of claim 5,
wherein the signal analyzing controller is further configured to corroborate a diagnosis of the at least one annotated region of each physiological signal based on context aware information appended to each physiological signal, the context aware information comprising information related to an operational and environment context within which a physiological sensor of the plurality of physiological sensors associated with each physiological signal is generating the physiological signal.

7. A central signal segregation system, comprising:
a central signal segregation station, and
a plurality of physiological sensors providing unknown signal types, wherein the plurality of physiological sensors of unknown signal types are configured to transmit a plurality of physiological signals of different types to the central signal segregation station, respectively,
   wherein, responsive to receiving the plurality of physiological signals, the central signal segregation station is configured to identify a particular type of each physiological signal, wherein identifying the particular type of each physiological signal comprises extracting a feature vector from the physiological signal, applying the feature vector to a plurality of physiological signal models derived from physiological sensors of known signal types obtain a similarity measurement for each physiological signal model, and choosing the physiological signal model providing a highest similarity.

8. The central signal segregation system of claim 7, wherein the plurality of physiological sensors of unknown signal types include at least two of an electrocardiogram monitor, a respiration electrode patch, a pulse oximeter, a blood pressure monitor, a galvanic skin response sensor, a skin temperature sensor, a heat flux sensor and a near body temperature sensor.

9. The central signal segregation system of claim 7, wherein the central signal segregation station comprises a signal analyzing controller configured to control an execution of a signal quality processing of each physiological signal based on the similarity measurement of the physiological signal, wherein the signal quality processing comprises a signal-to-noise quality measurement and/or a fiducial point detection.

10. The central signal segregation system of claim 9,
wherein the signal analyzing controller is further configured to control a communication to a physiological sensor associated with the physiological signal of the signal quality of the physiological signal.

11. The central signal segregation system of claim 7, wherein the central signal segregation station comprises a signal analyzing controller configured to annotate at least one region of each physiological signal, wherein the annotating comprises delineating at least one diagnostic region and at least one non-diagnostic region and generating an annotation of the at least one diagnostic region.

12. The central signal segregation system of claim 11,
wherein the signal analyzing controller is further configured to control a communication of a personalized care plan to a physiological sensor of the plurality of physicological sensors associated with the physiological signal, and
wherein the personalized care plan is derived from a trend diagnosis of physiological signals based on the annotations of the at least one region of each physiological signal.

13. The central signal segregation system of claim 12,
wherein the signal analyzing controller is further configured to corroborate a diagnosis of the at least one annotated region of each physiological signal based on context aware information appended to each physiological signal, the context aware information comprising information related to an operational and environment context within which a physiological sensor of the physiological sensors associated with each physiological signal is generating the physiological signal.

14. A central signal segregation method, comprising:
receiving a plurality of different physiological signals of unknown signal types from a plurality of physiological sensors providing unknown signal types; and
extracting a feature vector from each physiological signal of the plurality of different physiological signals of unknown signal types;
applying the feature vector to a plurality of physiological signal models derived from physiological sensors of known signal types to obtain a similarity measurement for each physiological signal model;
choosing the physiological signal model providing a highest similarity measurement for each physiological signal of the plurality of different physiological signals of unknown signal types; and
identifying a particular type of each physiological signal of the plurality of different physiological signals of unknown signal types using the chosen physiological signal model.

15. The central signal segregation method of claim 14, further comprising:
performing signal quality processing of each physiological signal for which the particular type is identified.

16. The central signal segregation method of claim 15, further comprising:
communicating to an associated physiological sensor of the plurality of physiological sensors a signal quality of each physiological signal based on the signal quality processing.

17. The central signal segregation method of claim 14, further comprising:
annotating at least one region of each physiological signal by delineating at least one diagnostic region and at least one non-diagnostic region, and generating an annotation of the at least one diagnostic region.

18. The central signal segregation method of claim 17, further comprising:
communicating a personalized care plan to an associated physiological sensor of the plurality of physiological sensors associated with each physiological signal, wherein the personalized care plan is derived from a trend diagnosis of physiological signals based on the annotations of the least one region of each physiological signal.

19. The central signal segregation method of claim 18, further comprising:
corroborating a diagnosis of the at least one annotated region of each physiological signal based on context aware information appended to each physiological signal, the context aware information comprising information related to an operational and environment context within which a physiological sensor of the plurality of physiological sensors associated with each physiological signal is generating the physiological signal.

20. The central signal segregation method of claim 17, further comprising:
corroborating a diagnosis of the at least one annotated region of each physiological signal based on context aware information appended to each physiological signal, the context aware information comprising information related to an operational and environment context within which a physiological sensor of the plurality of physiological sensors associated with each physiological signal is generating the physiological signal.

* * * * *